United States Patent
Lin

(10) Patent No.: US 11,110,107 B2
(45) Date of Patent: *Sep. 7, 2021

(54) METHODS FOR TREATMENT OF CANCER BY TARGETING SIRT5

(71) Applicant: Cornell University, Ithaca, NY (US)

(72) Inventor: Hening Lin, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 11 days.

This patent is subject to a terminal disclaimer.

(21) Appl. No.: 16/414,912

(22) Filed: May 17, 2019

(65) Prior Publication Data

US 2019/0298747 A1  Oct. 3, 2019

Related U.S. Application Data

(63) Continuation of application No. 14/342,925, filed as application No. PCT/US2012/054088 on Sep. 7, 2012, now Pat. No. 10,342,814.

(60) Provisional application No. 61/531,671, filed on Sep. 7, 2011.

(51) Int. Cl.
| | |
|---|---|
| *A61K 31/7016* | (2006.01) |
| *A61K 31/198* | (2006.01) |
| *C07K 14/47* | (2006.01) |
| *A61K 31/7088* | (2006.01) |
| *A61K 38/17* | (2006.01) |
| *A61K 31/713* | (2006.01) |
| *C07K 7/06* | (2006.01) |
| *C12N 15/113* | (2010.01) |
| *A61K 31/702* | (2006.01) |
| *A61K 38/02* | (2006.01) |
| *A61K 38/03* | (2006.01) |
| *A61K 38/00* | (2006.01) |

(52) U.S. Cl.
CPC ........ *A61K 31/7016* (2013.01); *A61K 31/198* (2013.01); *A61K 31/702* (2013.01); *A61K 31/7088* (2013.01); *A61K 31/713* (2013.01); *A61K 38/02* (2013.01); *A61K 38/03* (2013.01); *A61K 38/1709* (2013.01); *C07K 7/06* (2013.01); *C07K 14/47* (2013.01); *C12N 15/1137* (2013.01); *A61K 38/00* (2013.01); *C12N 2310/14* (2013.01); *C12Y 305/01098* (2013.01)

(58) Field of Classification Search
CPC ... A61K 31/7016; A61K 31/198; C07K 14/47
See application file for complete search history.

(56) References Cited

U.S. PATENT DOCUMENTS

| | | |
|---|---|---|
| 9,932,621 B2 | 4/2018 | Lin |
| 2009/0105246 A1 | 4/2009 | Bemis et al. |

FOREIGN PATENT DOCUMENTS

| | | |
|---|---|---|
| EP | 2 014 281 A1 | 1/2009 |
| WO | 2009/049018 A1 | 4/2009 |
| WO | 2012/006391 A2 | 1/2012 |

OTHER PUBLICATIONS

Boddapati, S.V. et al., "Organelle-Targeted Nanocarriers: Specific Delivery of Liposomal Ceramide to Mitochondria Enhances Its Cytotoxicity in Vitro and in Vivo" Nano Lett (Aug. 2008) pp. 2559-2563, vol. 2, No. 8.
Du, J. et al., "Sirt5 Is a NAD-Dependent Protein Lysine Demalonylase and Desuccinylase" Science (2011) pp. 806-809, vol. 334.
Haigis, M.C. et al., "SIRT4 Inhibits Glutamate Dehydrogenase and Opposes the Effects of Calorie restriction in Pancreatic Beta Cells" Cell (Sep. 8, 2006) pp. 941-954, vol. 126.
Heltvveg, B. et al., "Antitumor Activity of a Small-Molecule Inhibitor of Human Silent Information Regulator 2 Enzymes" Cancer Research (2006) pp. 4368-4377, vol. 66.
Kalle, A.M. et al., "Inhibition of SIRT1 by a small molecule induces apoptosis in breast cancer cells" Biochemical and Biophysical Research Communications (2010) pp. 13-19, vol. 401.
Lara, E. et al., "Salermide, a Sirtuin inhibitor with a Strong Cancer-Specific Proapoptotic Effect" Oncogene (2009) pp. 781-791, vol. 28.
Michan, S. et al., "Sirtuins in Mammals: insights into their biological function" Biochem. J. (2007) pp. 1-13, vol. 404.
Michishita, E. et al., "Evolutionarily Conserved and Nonconserved Cellular Localizations and Functions of Human SIRT Proteins" Mol. Biol. Cell (Oct. 2005) pp. 4623-4635, vol. 16.
Michishita, E. et al., "SIRT6 is a histone H3 lysine 9 deacetylase that modulates telomeric chromatin" Nature (Mar. 27, 2008) pp. 492-496, vol. 452.
Ota, H. et al., "Sirt1 inhibitor, Sirtinol, induces senescence-like growth arrest with attenuated Ras-MAPK signaling in human cancer cells" Oncogene (2006) pp. 176-185, vol. 25.
Paddison, P.J. et al., "Stable Suppression of Gene Expression by RNAi in Mammalian Cells" Proc Natl Acad Sci USA (Feb. 5, 2002) pp. 1443-1448, vol. 99, No. 3.
Sah, D., "Therapeutic potential of RNA Interference for neurological Disorders" Life Sciences (2006) pp. 1773-1780, vol. 79, No. 19.
Sauve, A.A. et al. "The Biochemistry of Sirtuins" Annu. Rev. Biochem. (2006) pp. 435-465, vol. 75.
Schuetz, A. et al., "Structural Basis of Inhibition of the Human NAD+-Dependent Deacetylase SIRT5 by Suramin" Structure (Mar. 2007) pp. 377-389, vol. 15.

(Continued)

*Primary Examiner* — Yong S. Chong

(74) *Attorney, Agent, or Firm* — Scully, Scott, Murphy & Presser, P.C.

(57) ABSTRACT

This disclosure demonstrates that inhibition of Sirt5 can suppress malignant transformation of cells. Therefore, methods of treating cancer based on inhibition of Sirt5 are disclosed.

5 Claims, 6 Drawing Sheets

Specification includes a Sequence Listing.

(56) References Cited

OTHER PUBLICATIONS

Smith, R.A. et al., "Delivery of Bioactive Molecules to Mitochondria in vivo" PNAS (Apr. 29, 2003) pp. 5407-5412, vol. 100, No. 9.

Verdin, E. et al., "Sirtuin Regulation of Mitochondria: Energy Production, Apoptosis, and Signaling" Trends Biochem. Sci. (Dec. 2010) pp. 669-675, vol. 35, No. 12.

Wang, J.B. et al., "Targeting Mitochondrial Glutaminase Ativity Inhibits Oncogenic Transformation" Cancer Cell (Sep. 14, 2010) pp. 207-209, vol. 18.

Zender, L et al., "Caspase 8 small Interfering RNA prevents Acute Liver Failure in Mice" Proc Natl Acad Sci USA (Jun. 24, 2003) pp. 7797-7802, vol. 100, No. 13.

Zhang, Y. Y et al., "Identification of a small molecule SIRT2 inhibitor with Selective tumor cytotoxicity" Biochem. Biophys. Res. Commun. (2009) pp. 729-733, vol. 386.

Schlicker, C. et al., "Substrated and Regulation Mechanisms for the Human Mitochondrial Sirtuins Sirts3 and Sirt5" J. Mol. Biol. (2008) pp. 790-801, vol. 382.

Smith, B.C. et al., "Mechanism-based Inhibition of Sir2 Deacetylases by Thioacetyl-Lysine Peptide" Biochemistry (2007) pp. 14478-14486, vol. 46.

Dong, L.F. et al., "Mitochondrial Targeting of Vitamin E Succinate Enhanced Its Pro-apoptotic and Anti-cancer Activity via Mitochondrial Complex II" Journal of Biological Chemistry (Feb. 4, 2011) pp. 3717-3728, vol. 286, No. 5.

He, B. et al., "Thiosuccinyl Peptides as Sirt5-Specific Inhibitors" J. Am. Chem.Soc. (2012) pp. 1922-1925, vol. 134.

McGlynn, L. et al., "Evaluating the Role of Sirtuins 5, 6 & 7 in Breast Cancer" Cancer Research (Dec. 15, 2009) vol. 69, No. 24.

Auwerx, J., "RMSSHMP-Role of the Mitochondrial Sirtuins, SIRT3 and SIRT5, in Hepatic Metabolism and Pathology" (Feb. 1, 2011).

Xie, Q.R. et al., "Sirtuin Expression is Downregulated in non-small cell lung cancer" The FASEB Journal (Apr. 2010), vol. 24, Abstract No. 567.3.

International Search Report dated Dec. 13, 2012 issued in International Application No. PCT/US2012/054088.

Chinese Office Action dated Mar. 21, 2016 issued in CN Patent Application No. 201280054564.2, with English-language translation.

Xie H., "Study on Function of SIRT5 and its Regulation on STAT3 Acetylation", China Master's Theses Full-text Database, Basic Science, (2011), pp. A006-A021, with English Abstract.

Deacetylation:

Demalonylation/desuccinylation:

n = 1: malonyl
n = 2: succinyl

METHODS FOR TREATMENT OF CANCER BY TARGETING SIRT5

CROSS REFERENCE TO RELATED APPLICATIONS

The present application is a continuation application of U.S. patent application Ser. No. 14/342,925, filed Mar. 5, 2014, which is the National Phase of PCT/US2012/054088, filed Sep. 7, 2012, which claims the benefit of U.S. Provisional Patent No. 61/531,671, filed Sep. 7, 2011, the entire contents of which are incorporated herein by reference.

STATEMENT REGARDING FEDERALLY SPONSORED RESEARCH OR DEVELOPMENT

This invention was made with Government Support under Contract No. GM086703 and CA163255, awarded by the National Institutes of Health. The Government has certain rights in this invention.

FIELD OF THE DISCLOSURE

This disclosure identifies a new target for cancer therapy. More specifically, this disclosure relates to cancer therapy based on inhibition of Sirt5.

BACKGROUND ART

Sirtuins are a class of evolutionarily conserved enzymes with NAD-dependent protein deacetylase activity (FIG. 1) (Sauve et al., *Annum. Rev. Biochem.* 75: 435-465 (2006), Michan et al., *Biochem. J.* 404: 1-13 (2007)). Since the initial reports that sirtuins exhibit deacetylase activity, they have been implicated in a number of cellular and biological functions including the regulation of life span, transcription, and metabolism (Sauve et al., *Annu. Rev Biochem.* 75: 435-465 (2006), Michan et al., *Biochem. J.* 404: 1-13 (2007)). There are seven sirtuins in mammals, Sirt1-7; however, only Sirt1-3 have been shown to be capable of robust deacetylase activity. Sirt4 and 7 lack detectable deacetylase activity (Michishita et al., *Mol. Biol. Cell* 16:4623-4635 (2005), Haigis et al., *Cell* 126: 941-954 (2006)), whereas Sirt5 and Sirt6 were reported to have only weak activity (Michishita et al., *Mol. Biol. Cell* 16:4623-4635 (2005), Schuetz et al., *Structure* 15: 377-389 (2007), Schlicker et al., *J. Mol. Biol.* 382: 790-801 (2008), Michishita et al., *Nature* 452: 492-496 (2008)). It has been recently discovered that human Sirt5 is an NAD-dependent desuccinylase and demalonylase (Du et al., *Science* 334: 806-809, 2011). It has also been found that many mitochondrial metabolic enzymes are succinylated and Sirt5 can regulate the activity of certain enzymes by desuccinylation.

Some sirtuins have been suggested to play a role in cancer development or tumor suppression (Verdin et al., *Trends Biochem. Sci.* 35: 669-675 (2010), Ota et al., *Oncogene* 25: 176-185 (2005), Heltweg et al., *Cancer Res.* 66: 4368-4377 (2006), Lara et al., *Oncogene* 28: 781-791 (2008), Zhang et al., *Biochem. Biophys. Res. Commun.* 386: 729-733 (2009), Kalle et al., *Biochemical and Biophysical Research Communications* 401: 13-19 (2010)). It is still not clear whether inhibiting sirtuins and which sirtuins could be used as a potential anti-cancer therapy (Verdin et al., *Trends Biochem. Sci.* 35: 669-675 (2010)).

SUMMARY OF THE DISCLOSURE

This disclosure has established Sirt5 as a new target for cancer therapy. Therefore, methods and compositions for treating cancer based on inhibition of Sirt5 are provided herein.

In one aspect, this disclosure is directed to a method of treating cancer in a subject by administration of an effective amount of a Sirt5 inhibitor to the subject.

In some embodiments, the Sirt5 inhibitor is a nucleic acid molecule. In certain embodiments, the nucleic acid molecule is an siRNA molecule or a vector capable of expressing the siRNA molecule. In a specific embodiment, the siRNA molecule is selected from the group consisting of siRNA1, siRNA2, siRNA3, siRNA4, siRNA5 and siRNA 6, as described herein.

In other embodiments, the Sirt5 inhibitor is a small molecule compound. In certain embodiments, the small molecule compound is a lysine-containing thiosuccinyl or thiomalony peptide. In specific embodiments, the small molecule compound is represented by the formula

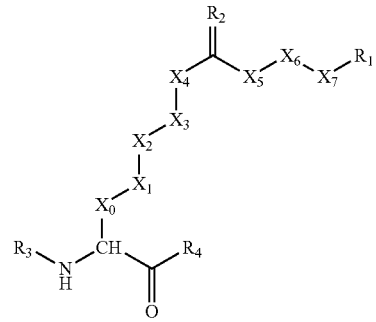

wherein:
$R_1$ is an anionic or ionizable group;
$R_2$ is selected from S, $NR_5$, and O, wherein $R_5$ is H, methyl, ethyl, isopropyl, phenyl, or benzyl;
when $R_1$ is carboxyl, then $R_2$ is not O, and when $R_2$ is O, then $R_1$ is not carboxyl;
$X_0$, $X_1$, $X_2$, $X_3$, $X_4$, $X_5$, $X_6$ and $X_7$ are independently selected from —$(CH_2)_n$— (wherein n represents 1, 2, or 3), —$NR_5$—, —O—, —S—, or a bond, provided that at least one of $X_0$-$X_4$ is not a bond, and at least one of $X_5$-$X_7$ is not a bond;
$R_3$ and $R_4$ are independently selected from H, hydrocarbon (R), amino acid, dipeptide, tripeptide, oligopeptide, protein, nucleobase, nucleotide, dinucleotide, trinucleotide, oligonucleotide, monosaccharide, disaccharide, oligosaccharide, and protecting groups or a combination thereof or modified form thereof.

Other Sirt5 inhibitors include nucleic acid or peptide aptamers, and anti-Sirt5 antibodies.

In certain embodiments, the Sirt5 inhibitors are prepared to permit mitochondria targeted delivery.

In another aspect, pharmaceutical compositions useful for treating cancer are provided which include a Sirt5 inhibitor.

BRIEF DESCRIPTION OF THE DRAWINGS

FIG. 3A: RT-PCR results showing that Sirt5 is knocked down by both siRNA in SKBR3 (a breast cancer cell line) and U87 (a brain cancer cell line) cells. FIG. 3B: Soft-agar assay demonstrating that Sirt5 knockdown inhibits the anchorage-independent growth in both cancer cell lines. FIG. 3C: Serum-limitation assay demonstrating that Sirt5 knockdown inhibit cancer cells (SKBR3 and U87), but not normal cells (MCF10A). FIG. 3D: Sirt1 was successfully knocked down as demonstrated by a Western blot (left), but soft-agar assay (right) demonstrated that Sirt1 knockdown has no obvious effects on the anchorage-independent growth of SKBR3 cancer cells.

DETAILED DESCRIPTION

Figure 1:
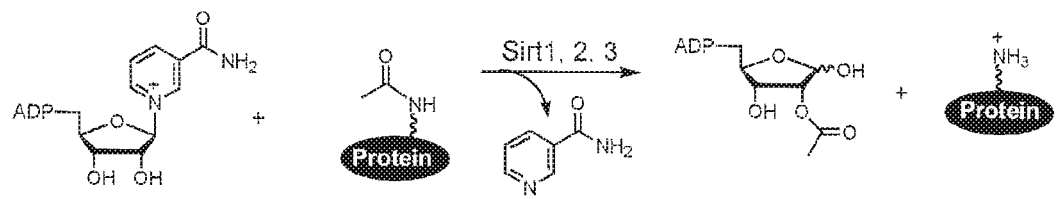
FIG. 1. NAD-dependent deacetylation, demalonylation, and desuccinylation catalyzed by different human sirtuins.
Figure 1:
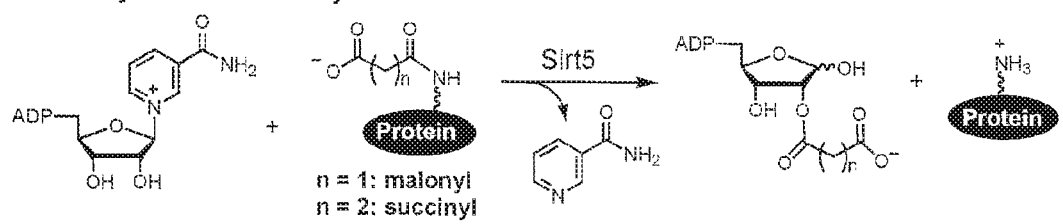

It has been demonstrated herein that inhibition of Sirt5 can suppress malignant transformation of cells. Thus, this disclosure provides a new target for cancer therapy. Methods and compositions for treating cancer based on inhibition of Sirt5 are provided herein.

By "treating a cancer" it means that the cancer development, growth, and/or metastasis is significantly inhibited, as reflected by reduced or delayed cancer appearances or relapses, reduced tumor volumes or number of cancerous cells, a reduced extent of increase in tumor volume or cancerous cells, and/or reduced occurrences of metastasis. Tumor growth can be determined, e.g., by examining the tumor volume via routine procedures (such as obtaining two-dimensional measurements with a dial caliper). Tumor metastasis can be determined by examining the appearance of tumor cells in secondary sites or examining the metastatic potential of biopsied tumor cells in vitro using various laboratory procedures.

Cancers which can be treated by using the methods disclosed herein based on inhibition of Sirt5 include, but are not limited to, melanoma, lymphoma, plasmocytoma, sarcoma, glioma, thymoma, leukemia, breast cancer, prostate cancer, colon cancer, esophageal cancer, brain cancer, lung cancer, ovary cancer, cervical cancer, hepatoma, and other neoplasms known in the art.

By "inhibition of Sirt5", it is meant that the expression of the Sirt5 gene, the production of the Sirt5 protein, and/or an enzymatic activity of the Sirt5 protein, is inhibited, suppressed, reduced or even eliminated.

"Sirt5 enzymatic activities", as used herein, include enzymatic removal of acyl groups (malonyl, succinyl, glutaryl, and acetyl) from lysine residues. Thus, Sirt5 activities include demalonylation, desuccinylation, deglutarylation, and deacetylation of lysine residues. In specific embodiments, inhibition of Sirt5 results in inhibition of at least the desuccinylase and demalonylase activities of Sirt5. "Sirt5 desuccinylase activity" refers to Sirt5 enzymatic removal of a succinyl group from a lysine residue. "Sirt5 demalonylase activity" refers to Sirt5 enzymatic removal of a malonyl group from a lysine residue. Sirt5 can act on a stand-alone lysine residue with an acyl group, or on an acylated lysine residue in a peptide or protein. Sirt5 activities, for example, the desuccinylase and demalonylase activities, can occur in vivo as a posttranslational modification of proteins containing succinylated or malonylated lysines, resulting in the generation of downstream physiological events.

As used herein, the term "Sirt5 inhibitor" includes molecules that achieves inhibition of Sirt5, such as a nucleic acid molecule which reduces the level or inhibits the activity of a Sirt5 mRNA, an oligopeptide, a small molecule inhibitory compound, an aptamer, and an antibody that specifically binds the Sirt5 protein, such that an enzymatic activity of Sirt5 (for example, NAD-dependent desuccinylation and demalonylation activities) is effectively suppressed or reduced in the cells being treated. A reduction is considered significant, for example, if the reduction is at least about 20%, and in some embodiments at least about 30%, 40% or 50%, and in other embodiments at least about 70%, 80%, 90% or greater. Sirt5 inhibitors are preferable Sirt5-specific inhibitors, i.e., which inhibit Sirt5 without significantly affecting other sirtuins.

In one embodiment, the cancer therapeutic method employs a Sirt5 inhibitor that is a nucleic acid molecule. Such nucleic acid molecule includes an antisense RNA, a siRNA, a miRNA (or "microRNA"), or a transgene which codes for and is capable of expressing any such RNA molecule in the target tissue of a recipient. An antisense RNA is an RNA molecule that is complementary to endogenous mRNA and blocks translation from the endogenous mRNA by forming a duplex with the endogenous mRNA. An antisense RNA should be at least about 10 nucleotides, preferably, at least about 15 or 17 nucleotides, more preferably, at least about 50 nucleotides. siRNAs are small (typically 20-25 nucleotides in length) double-stranded RNAs which are known to be involved in the RNA interference pathway and interfere with the expression of a specific gene. Given the sequence of a target gene, siRNAs can be designed, and made either synthetically or in cells from an exogenously introduced vector (e.g., a plasmid) to achieve suppression of expression of a gene of interest. Similar to siRNAs, miRNAs are also small RNA molecules (generally about 21-22 nucleotides) that regulate gene expression. miRNAs are processed from long precursors transcribed from non-protein-encoding genes, and interrupt translation through imprecise base-pairing with target mRNAs. miRNA can be designed and introduced to cells or tissues to target and suppress the expression of a gene of interest using techniques documented in the art.

In some embodiments, the Sirt5 inhibitor is a Sirt5 siRNA molecule. The effectiveness of an siRNA molecule can be tested and confirmed in cultured cells prior to use in a cancer recipient, to determine whether a Sirt5 mRNA has been "silenced" or the Sirt5 gene has been "knocked down", as illustrated in Example 1 below. Illustrative examples of Sirt5 siRNA molecules include:

```
siRNA1
                                         (SEQ ID NO: 3)
5'-CCA GCG UCC ACA CGA AAC CAG AUU U-3'

(SEQ ID NO: 4)
5'-AAA UCU GGU UUC UGG GUG ACG CUG G-3' siRNA2
                                         (SEQ ID NO: 5)
5'-CCA AGU CGA UUG AUU UCC CAG CUA U-3'

(SEQ ID NO: 6)
5'-AUA GCU GGG AAA UCA AUC GAC UUG G-3' siRNA3
                                         (SEQ ID NO: 7)
5'-UGC AAA AGC AAA GCA CAU AGU CAU C-3'

(SEQ ID NO: 8)
5'-GAU GAC UAU GUG CUU UGC UUU UGC A-3' siRNA4
                                         (SEQ ID NO: 9)
5'-ACC CGU CCC GGG UGU GGG AGU UCU A-3'

(SEQ ID NO: 10)
5'-UAG AAC UCC CAC ACC CGG GAC GGG U-3' siRNA5
                                        (SEQ ID NO: 11)
5'-CUC GAU GUA CCU CUU GUG GAG UUG U-3'

(SEQ ID NO: 12)
5'-ACA ACU CCA CAA GAG GUA CAU CGA G-3' siRNA6
                                        (SEQ ID NO: 13)
5'-AAA CUU CCC CGG UGU GAA GAG GCA G-3'

(SEQ ID NO: 14)
5'-CUG CCU CUU CAC ACC GGG GAA GUU U-3'
```

A nucleic acid Sirt5 inhibitor molecule such as an antisense RNA, siRNA, or miRNA, can be delivered directly to the target tissue of a recipient. Successful delivery of siRNAs, including in clinical settings, has been documented in the art (Paddison et al., *Proc Natl Acad Sci USA* 99(3): 1443-1448 (2002), Sah, *Life Sci* 79 (19): 1773-1780 (2006), Zender et al., *Proc Natl Acad Sci USA* 100(13): 7797-802 (2003)). Alternatively, an inhibitory RNA molecule can be expressed from a vector carrying a transgene which codes for such RNA molecule, which vector is delivered to the target tissue of a recipient. Suitable vectors include any vectors useful for gene therapy, for example, plasmids, cosmids, viruses (bacteriophage, animal viruses, and plant viruses), and artificial chromosomes (e.g., YACs). Viral vectors include e.g., retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors, adeno-associated viral (AAV) vectors, simian virus 40 (SV-40) vectors, bovine papilloma virus vectors. Epstein-Barr virus vectors, herpes virus vectors, vaccinia virus vectors, Harvey murine sarcoma virus vectors, murine mammary tumor virus vectors, and Rous sarcoma virus vectors.

In other embodiments, the cancer therapy method utilizes a thiosuccinyl or a thiomalonyl peptide. Thiosuccinyl or thiomalonyl peptides can inhibit Sirt5 desuccinylase and demalonylase activities by forming a stalled covalent intermediate. These peptides can undergo the first step of the Sirt5-catalyzed reaction, forming a covalent intermediate which cannot proceed further. Because other sirtuins do not recognize malonyl and succinyl lysine peptides, thiomalonyl and thiosuccinyl peptides are Sirt5-specific inhibitors.

In specific embodiments, the Sirt5 inhibitor is a small molecule compound. As used herein, "small molecules" include organic compounds, organometallic compounds, salts of organic and organometallic compounds, saccharides, amino acids, and nucleotides. Small molecules typically have molecular weights less than approximately 1200 Daltons, in some embodiments less than 1000, 800 or even 500 Daltons. Small molecules include compounds that are found in nature as well as synthetic compounds. The compounds may be modified to enhance, for example, efficacy, stability, or pharmaceutical compatibility.

Sirt5 inhibitor compounds considered herein can be described by the following generic formula:

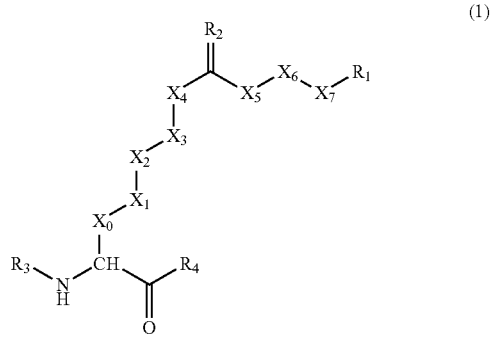

(1)

In Formula (1), $R_1$ is a negatively-charged (i.e., anionic) or ionizable group. Some examples of negatively-charged or ionizable groups include carboxylate (—COO$^-$), carboxylic acid (—COOH), thiocarboxylate (—CSO$^-$), sulfonate (—SO$_3^-$), phosphonate (—PO$_3^{2-}$), and nitro (—NO$_2$) groups. The group $R_2$ is selected from S, NR$_5$, and O, wherein $R_5$ can be a hydrogen atom (H) or a hydrocarbon group containing one to seven carbon atoms (e.g., methyl, ethyl, isopropyl, phenyl, or benzyl). The groups $X_0$, $X_1$, $X_2$, $X_3$, $X_4$, $X_5$, $X_6$ and $X_7$ are independently selected from —(CH$_2$)$_n$— (wherein n represents 1, 2, or 3), —NR$_5$—, —O—, —S—, or a bond, provided that at least one of $X_0$-$X_4$ is not a bond, and at least one of $X_5$-$X_7$ is not a bond. Generally, $X_5$, $X_6$, and $X_7$ are —CH$_2$— groups or a bond, provided that at least one of $X_5$-$X_7$ is not a bond. Often, at least one, two, three, or all four of $X_0$-$X_3$ are —CH$_2$— groups, while $X_4$ is selected from —CH$_2$—, —NR$_5$—, —O—, or —S— groups. In specific embodiments, all four of $X_0$—$X_3$ are —CH$_2$— groups, while $X_4$ is selected from —CH$_2$—, —NR$_5$—, —O—, or —S— groups, and $X_5$-$X_7$ are —CH$_2$— groups or a bond, provided that at least one of $X_5$-$X_7$ is not a bond. The groups $R_3$ and $R_4$ are independently selected from H, hydrocarbon (R), amino acid, dipeptide, tripeptide, oligopeptide (e.g., from 4, 5, 6, 8, 10, 12, or 15 amino acid residues up to 20, 25, 30, 35, 40, 45, or 50 amino acid residues), protein, nucleobase, nucleotide, dinucleotide, trinucleotide, oligonucleotide, monosaccharide, disaccharide, oligosaccharide, and protecting groups (e.g., tBOC or FMOC groups), or a combination thereof or modified form thereof (e.g., lipoprotein or nucleoprotein), wherein $R_4$ may also be a —OR, —NHR, or —NC(O)R group, and $R_3$ may also be a —C(O)R or —C(O)NHR group. Generally, when $R_1$ is carboxyl, then $R_2$ is not O, and when $R_2$ is O, then $R_1$ is not carboxyl.

In particular embodiments of Formula (1), $R_2$ is S, thus resulting in a sub-generic set of compounds of the following formula:

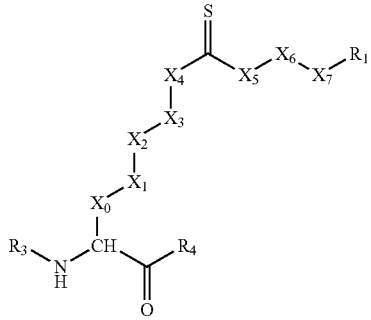

(1a)

In other particular embodiments of Formula (1), $R_2$ is S and $R_1$ is carboxyl, thus resulting in a sub-generic set of compounds of the following formula:

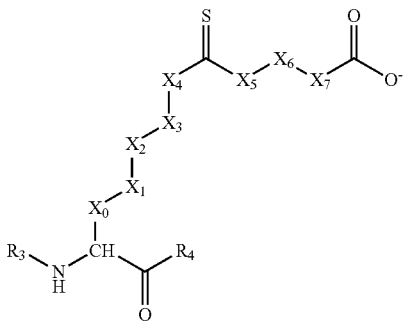

(1b)

In still other particular embodiments of Formula (1), $R_2$ is S, $R_1$ is carboxyl, and $X_4$ is —$NR_5$—, thus resulting in a sub-generic set of compounds of the following formula:

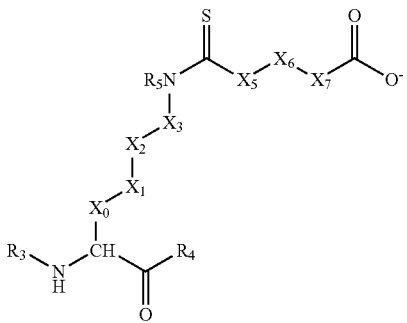

(1c)

In Formula (1c), $X_0$-$X_3$ are preferably selected from —$(CH_2)_n$— groups (wherein n represents 1, 2, or 3) or a bond, wherein at least one of $X_0$-$X_3$ is not a bond; and $X_5$-$X_7$ are preferably —$CH_2$— groups or a bond, and at least one of $X_5$-$X_7$ is not a bond. In specific embodiments, all four of $X_0$-$X_3$ are —$CH_2$— groups, and $X_5$-$X_7$ are $CH_2$— groups or a bond provided at least one of $X_5$-$X_7$ is not a bond.

The double-bonded group $R_2$ in Formula (1) may alternatively be replaced with two single-bonded groups ($R_5$ and $R_6$), as shown in the following sub-formula:

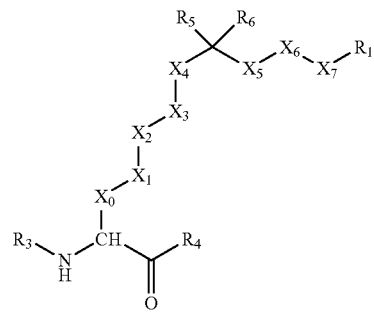

(2)

In Formula (2), $R_5$ and $R_6$ are independently selected from H, a hydrocarbon group (R) having one to six carbon atoms, OH, OR, SH, SR, and NHR, except that, generally, both of $R_5$ and $R_6$ are not selected from OH, OR, SH, SR, and NHR (i.e., if one of $R_5$ and $R_6$ is OH, OR, SH, SR, or NHR, then the other of $R_5$ and $R_6$ is H or R). In some embodiments, when one of $R_5$ and $R_6$ is a OH or OR group, then $R_1$ is not a carboxyl group.

The terms "hydrocarbon group" and "hydrocarbon linker", as used herein, are, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, or eighteen carbon atoms, or a particular range of carbon atoms between any of the foregoing carbon numbers.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene, i.e., —$CH_2$—, or methine linkers), ethyl (or ethylene or dimethylene, i.e., —$CH_2CH_2$— linkers), n-propyl, n-butyl, n-pentyl, and n-hexyl groups.

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, and 3-methylpentyl. Some examples of branched alkylene linkers are those derived by removal of a hydrogen atom from one of the foregoing exemplary branched alkyl groups (e.g., isopropylene, —CH($CH_3$)$CH_2$—).

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, and cycloheptyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, 2-propen-1-yl (allyl), 3-buten-1-yl, 2-buten-1-yl, butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, and propargyl (2-propynyl). Some examples of straight-chained olefinic linkers are those derived by removal of a hydrogen atom from one of the foregoing exemplary straight-chained olefinic groups (e.g., vinylene, —CH═CH—, or vinylidene).

The hydrocarbon groups or linkers can alternatively be unsaturated and branched (i.e., branched olefinic or alkenyl groups or linkers). Some examples of branched olefinic groups include 2-propen-2-yl, 3-buten-2-yl, 3-buten-3-yl, 4-penten-2-yl, 4-penten-3-yl, 3-penten-2-yl, 3-penten-3-yl, and 2,4-pentadien-3-yl. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). Some examples of unsaturated and cyclic hydrocarbon groups include cyclopropenyl, cyclobutenyl, cyclopentenyl, cyclopentadienyl, cyclohexenyl, cyclohexadienyl, phenyl, and benzyl. The unsaturated cyclic hydrocarbon group can also be a polycyclic (e.g., bicyclic) group by either possessing a bond between two of the ring groups (e.g., biphenyl) or a shared (i.e., fused) side (e.g., naphthalene, anthracene, phenanthrene, phenalene, and indene). Some examples of cycloalkenylene linkers are those derived by removal of a hydrogen atom from one of the foregoing exemplary cycloalkenyl groups (e.g., phenylene and biphenylene).

In some embodiments, one or more of the hydrocarbon groups or linkers may also include one or more heteroatoms (i.e., non-carbon and non-hydrogen atoms), such as one or more heteroatoms selected from oxygen, nitrogen, sulfur, halide, and phosphorus atoms. Some examples of oxygen-containing groups include hydroxyl (OH) groups, carbonyl groups (e.g., ketone, aldehyde, ester, amide, or urea functionalities), and carbon-oxygen-carbon (ether) groups. The ether group can also be a polyalkyleneoxide group, such as a polyethyleneoxide group. Some examples of nitrogen-containing groups include primary amine groups, secondary amine groups, tertiary amine groups, quaternary amine groups, cyanide group, amide group (i.e., —C(O)NR$_2$, wherein R is independently selected from hydrogen atom and hydrocarbon group, as described above), nitro group, urea group, imino group, and carbamate group, wherein it is understood that a quaternary amine group necessarily possesses a positive charge and requires a counteranion. Some examples of sulfur-containing groups include mercapto (i.e., —SH), thioether (i.e., sulfide), disulfide, sulfoxide, sulfone, sulfonate, and sulfate groups. Halide atoms considered herein include fluorine, chlorine, and bromine.

In a specific embodiment, the candidate compound is a thiosuccinyl compound. In a particular embodiment, the candidate compound is H3K9 thiosuccinyl (H3K9 TSu) peptide, represented by the sequence KQTAR(TSuK) STGGKA (SEQ ID NO: 15).

The synthesis of the inhibitor compounds described above relies on established and well-known methodologies of the art. For example, the coupling of malonate and succinylate to lysine side chains can be accomplished using well known reaction conditions for the preparation of amides from amines and carboxylic acids. The conversion of a carbonyl oxygen atom (e.g., R$_2$) to a thiocarbonyl can be accomplished by, for example, reaction with Lawensson reagent by methods well known in the art.

The effectiveness of a Sirt5 inhibitory compound can be tested and confirmed in in vitro assays, including, for example, the assay described in WO2012/006391A2 (incorporated herein by reference). Essentially, the assay is based on the use of a substrate containing a malonyl, succinyl or glutaryl lysine, linked to an indicator moiety (a fluorescent moiety). The linkage between the lysine and the indicator moiety can be severed by a cleavage agent (such as a protease, e.g., trypsin) which is sensitive to the state of malonylation, succinylation or glutarylation of the lysine residue. Thus, when the substrate is contacted with Sirt5 under conditions for Sirt5 to demalonylate, desuccinylate or deglutarylate the substrate, the removal of the acyl group (possibly leading to the exposure of the cleavage site) permits the cleavage agent to act on the cleavage site and releases the indicator moiety, which then generates a detectable signal (fluorescence). The presence of a Sirt5 inhibitor compound would reduce the amount of signal detected.

In another embodiment, the Sirt5 inhibitor is an aptamer that binds specifically to the Sirt5 protein and blocks the Sirt5 protein from interacting with its substrates. Aptamers are molecules, either nucleic acid or peptide, that bind to a specific target molecule. Nucleic acid aptamers are generally short strands of DNA or RNA that have been engineered through repeated rounds of in vitro selection known as SELEX (systematic evolution of ligands by exponential enrichment) to bind to various molecular targets. Peptide aptamers can be selected using various systems, most frequently through the yeast two hybrid system. Peptide aptamers generally consist of a variable peptide loop (typically composed of ten to twenty amino acids), attached at both ends to a protein scaffold. This double structural constraint greatly increases the binding affinity of the peptide aptamer to levels comparable to an antibody.

In other embodiments, the Sirt5 inhibitor is an anti-Sirt5 antibody that specifically binds to and blocks the Sirt5 protein from interacting with its substrates. Both monoclonal antibodies and polyclonal antibodies are suitable for use in the cancer treatment method of this invention.

Any of the Sirt5-inhibitors described herein, including nucleic acid inhibitors and small molecule inhibitors, can be made or modified to have improved properties for administration to a mammalian subject, e.g., to improve stability, cell penetrating ability, among others. For example, to enhance cell permeability of the substrate, the peptide chain can include a string of multiple amino acids (such as 8-10 arginine residues).

Sirt5 inhibitors described herein may be formulated in a conventional manner using one or more physiologically or pharmaceutically acceptable carriers or excipients. Examples of carriers include fats, oils, water, saline solutions, lipids, liposomes, resins, binders, fillers and the like, or combinations thereof. For example, Sirt5 inhibitory compounds and their physiologically acceptable salts and solvates may be formulated for administration by, for example, injection (e.g. SubQ, IM, IP, IV), inhalation or insufflation (either through the mouth or the nose), or oral, buccal, sublingual, transdermal, nasal, parenteral or rectal administration. In one embodiment, a Sirt5 inhibitory compound may be administered locally, at the site where the target cancerous cells are present, i.e., in a specific tissue, organ, or fluid (e.g., blood, cerebrospinal fluid, etc.). Sirt5 inhibitory compounds can be formulated for a variety of modes of administration, including systemic and topical or localized administration. Techniques and formulations generally may be found in Remington's Pharmaceutical Sciences, Meade Publishing Co., Easton, Pa.

Figure 6:
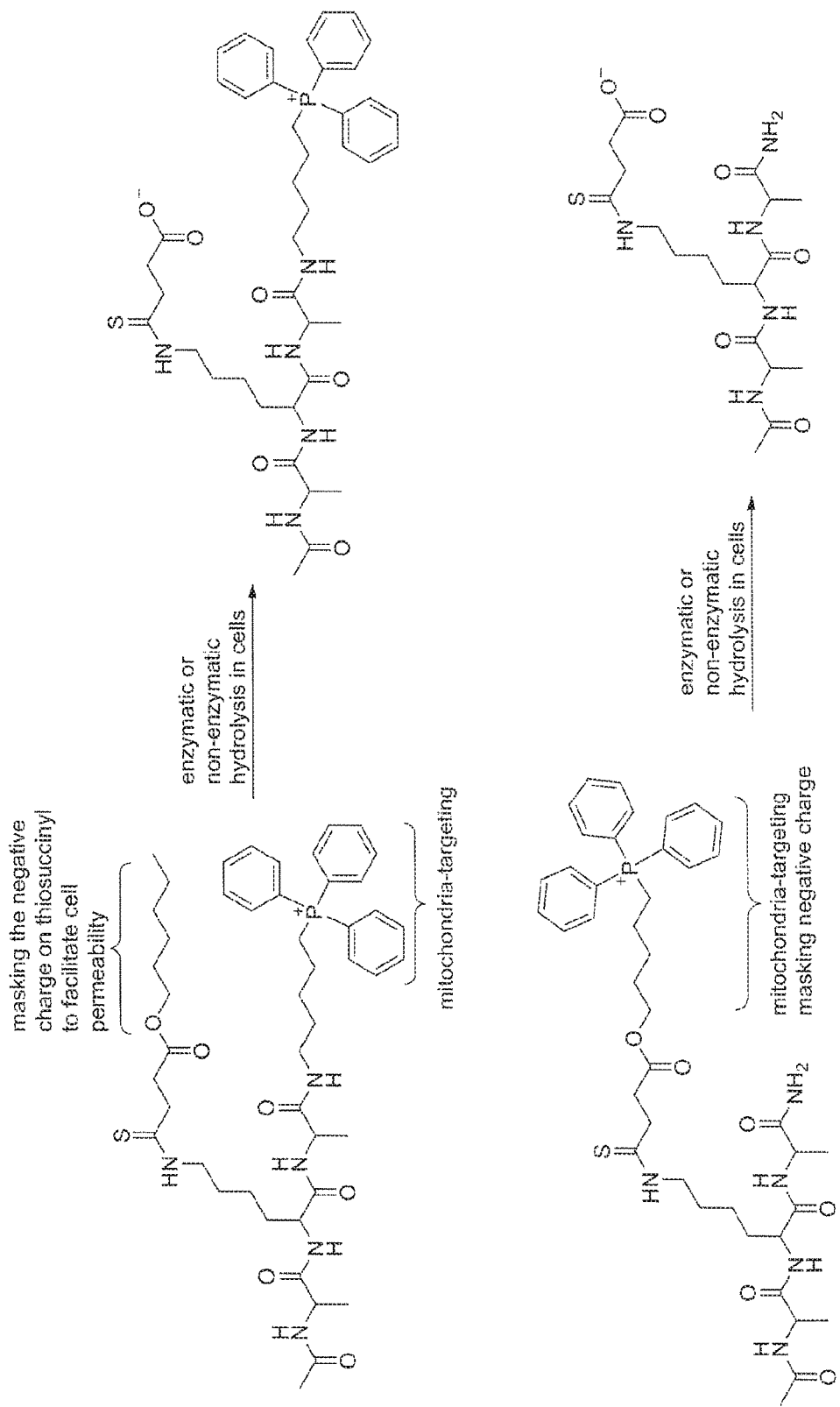
FIG. 6. Illustration of a thiosuccinyl peptide modified with a triphenylphosphonium cation for mitochondria delivery.

In a specific embodiment, a Sirt5 inhibitor is designed and prepared to achieve mitochondria-specific delivery. Sirt5 is known to be mainly localized in mitochondria. Thus, mitochondrial targeting of Sirt5 inhibitors can have improved efficiency in inhibiting Sirt5. It has been shown that a triphenylphosphonium cation can facilitate the targeting of small molecules and liposomes to mitochondria (see, e.g., Smith et al., PNAS 100: 5407-5412 (2003); Boddapati et al., Nano Lett 2008 August; 8(8):2559-63, Epub 2008 Jul. 9). For example, a triphenylphosphonium cation can be introduced into the structures of the inhibitors, which temporarily masks the negative charge on the inhibitors. Two specific examples using a thiosuccinyllysine peptide are shown in FIG. 6. In one example, the negative charge of thiosuccinyl is masked by forming a hexyl ester while the TPP cation is attached to the C-terminal of the peptide. In the other example, the masking of the negative charge and the introduction of TPP cation is achieved at the same time. The ester bond can be slowly hydrolyzed inside the cells, thus releasing the active Sirt5 inhibitor in the mitochondria.

Pharmaceutical compositions may comprise from about 0.00001 to 100% such as from 0.001 to 10% or from 0.1% to 5% by weight of one or more Sirt5-inhibitory compounds described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Toxicity and therapeutic efficacy of Sirt5-inhibitory compounds can be determined by standard pharmaceutical procedures in cell cultures or experimental animals. The $LD_{50}$ is the dose lethal to 50% of the population. The dose ratio between toxic and therapeutic effects ($LD_{50}/ED_{50}$) is the therapeutic index. Sirt5 inhibitors that exhibit large therapeutic indexes are preferred. While Sirt5 inhibitors that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

While the precise dosage of an inhibitor to be therapeutically effective can be determined by the skilled artisan, as a general rule, the therapeutically effective dosage of an inhibitor can be in the range of about 0.5 μg to about 2 grams per unit dosage form. A unit dosage form refers to physically discrete units suited as unitary dosages for mammalian treatment: each unit containing a pre determined quantity of the active material calculated to produce the desired therapeutic effect in association with any required pharmaceutical carrier. The methods of the present invention contemplate single as well as multiple administrations, given either simultaneously or over an extended period of time.

The present description is further illustrated by the following examples, which should not be construed as limiting in any way. The contents of all cited references (including literature references, issued patents, and published patent applications as cited throughout this application) are hereby expressly incorporated by reference.

Example-1

This Example describes experiments performed to examine whether Sirt5 is important for the malignant state of cancer cells.

Figure 2:
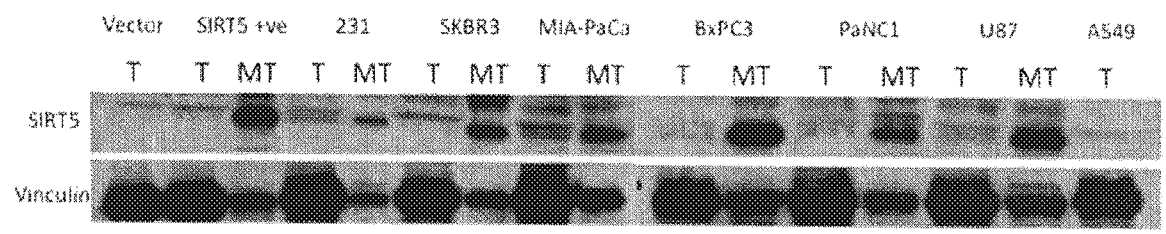
FIG. 2. Sirt5 was specifically present in the mitochondrial fractions from different human cancer cell lines. Total whole cell lysates (T) (25 µg of total protein) and mitochondrial fractions (MT) (25 µg of total protein) were analyzed in a Western blot analysis using a specific anti-Sirt5 antibody.

The inventors verified that Sirt5 was highly and specifically expressed in the mitochondria of a number of different cancer cell lines, including human breast cancer cells (SKBR3 and MDAMB231 cells), human pancreatic cancer cells (MIA-PaCA and PaNC1 cells), human glioblastoma (U87) cells, and human lung cancer (A549) cells (FIG. 2).

Two different short interfering RNA molecules were designed based on a Sirt5 variant cDNA sequence (SEQ ID NO: 1).

```
siRNA1
                                        (SEQ ID NO: 3)
5'-CCA GCG UCC ACA CGA AAC CAG AUU U-3'

(SEQ ID NO: 4)
5'-AAA UCU GGU UUC UGG GUG ACG CUG G-3' siRNA2
                                        (SEQ ID NO: 5)
5'-CCA AGU CGA UUG AUU UCC CAG CUA U-3'

(SEQ ID NO: 6)
5'-AUA GCU GGG AAA UCA AUC GAC UUG G-3'
```

Figures 3A, 3B:
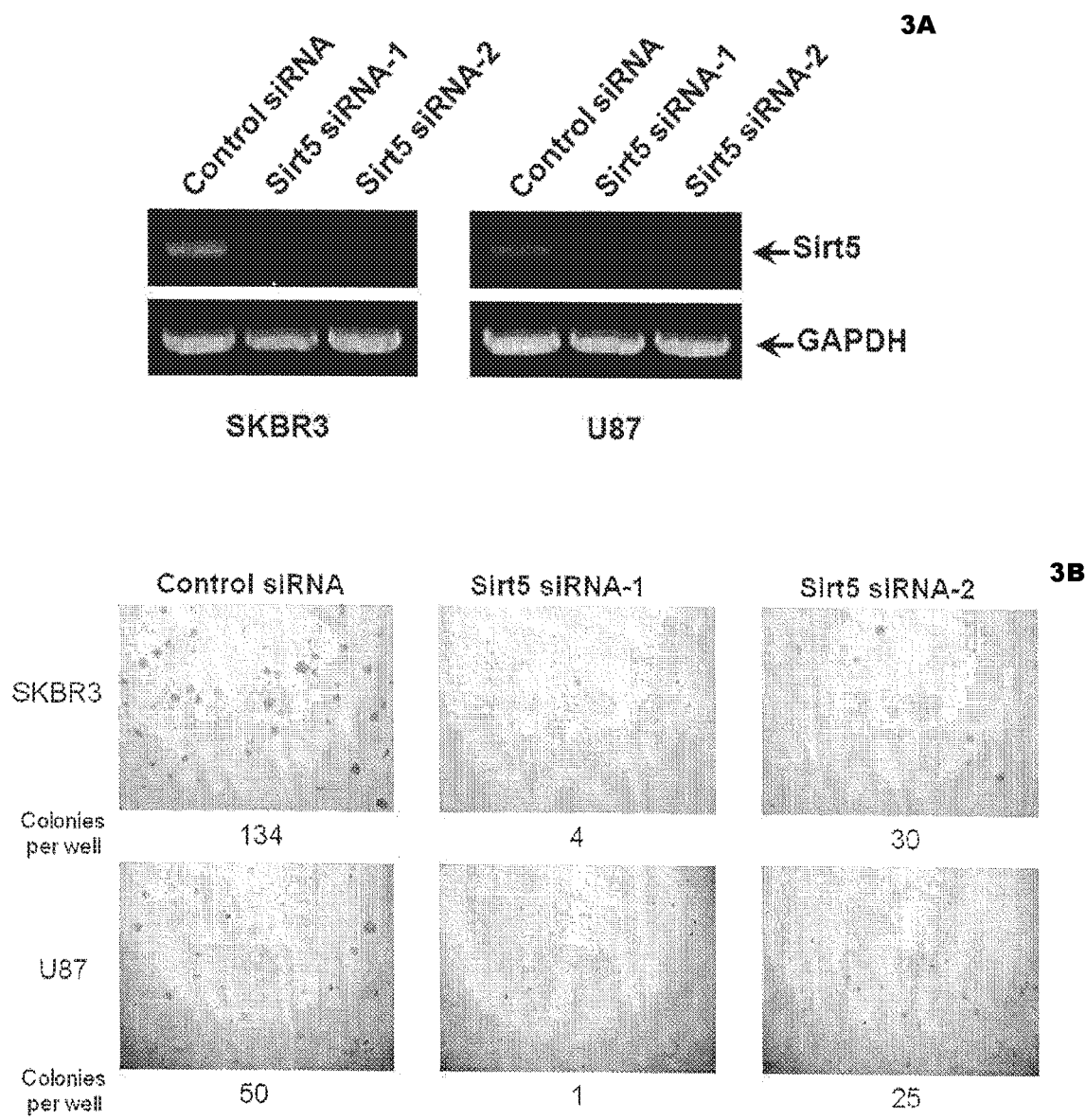
FIGS. 3A-3D. Sirt5 knockdown inhibits the growth of cancer cells.
Figures 3C, 3D:
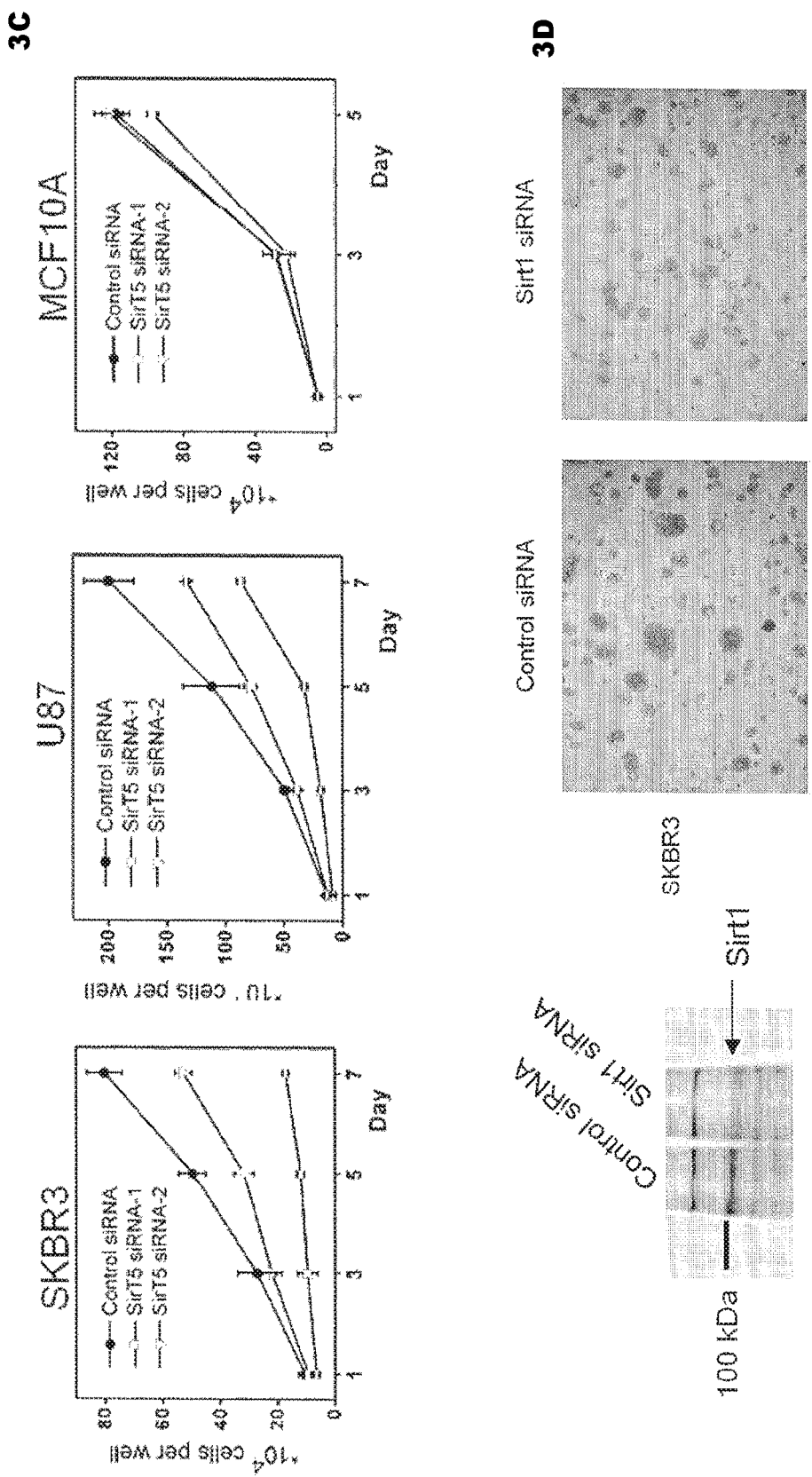

Knockdown of Sirt5 using each siRNA molecule was confirmed in RT-PCR (FIG. 3A), which resulted in inhibition of the transformed phenotype of cancer cells (monitored using soft agar assay to monitor the anchorage-independent growth, FIG. 3B). This was tested in several cancer cell lines, including a breast cancer cell line (SKBR3) and a brain cancer cell line (U87). A serum limitation assay (to examine the growth factor-independent proliferation of cells, FIG. 3C) also demonstrated that knockdown of Sirt5 significantly inhibited the transformed phenotype of cancerous cells. Furthermore, the inhibition of cell proliferation and growth was selective to cancer cells, as the growth of MCF10A cells (normal cells), was not significantly affected by Sirt5 knockdown (FIG. 3C). In contrast, knockdown of Sirt1 had no obvious effect on the anchorage-independent growth of SKBR3 cells (FIG. 3D), even though Western blot showed successful knockdown of Sirt1.

Example-2

Figure 4:
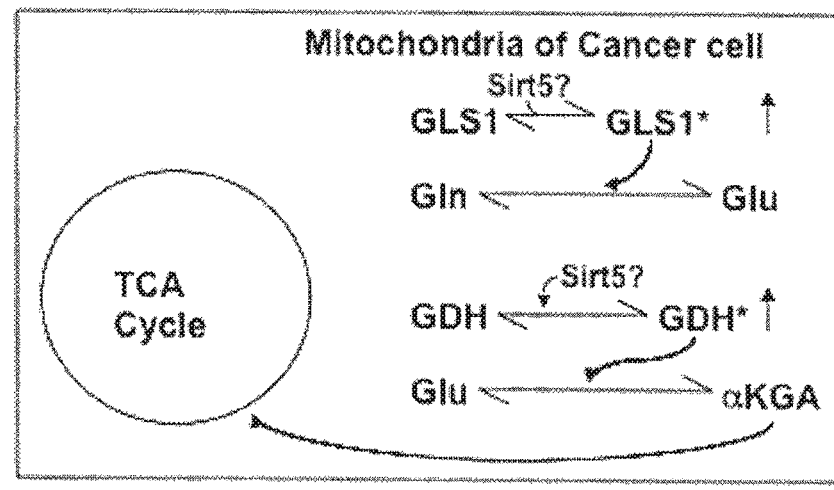
FIG. 4. A working model for elevated glutamine metabolism in cancer cells. Because of the Warburg effect, most of the pyruvate generated from the citric acid (TCA) cycle in cancer cells is converted to lactate, rather than acetyl-CoA and citrate. Thus, cancer cells rely on elevated glutamine (Gln) metabolism to help feed the TCA cycle. It is proposed herein that GLS1 and/or GDH are activated through desuccinylation catalyzed by Sirt5.

The inventors then examined whether knock-downs of Sirt5 might affect the activation of GLS1 in cancer cells. GLS1 is an enzyme at a key regulatory node in one of the two major chain of events that represent the metabolic changes accompanying malignant transformation. The first of these changes is the acceleration of various steps in the glycolytic pathway, which fall under the umbrella term of the "Warburg effect". A key outcome of these changes is that the normal product of the glycolytic pathway, pyruvate, is predominantly converted to lactic acid, rather than being converted to acetyl-CoA and ultimately to citrate to "kickstart" the citric acid cycle in the mitochondria. Because cancer cells use components from the citric acid cycle for various biosynthetic processes, and since the normal input into this cycle via pyruvate from the glycolytic pathway has been largely eliminated due to the Warburg effect, cancer cells require alternative inputs. One way in which this is achieved is through elevated glutamine metabolism, specifically, through the accelerated conversion of glutamine to glutamate via GLS1, followed by the production of α-ketoglutarate from glutamate as catalyzed by glutamate dehydrogenase (GDH) (FIG. 4).

Figure 5:
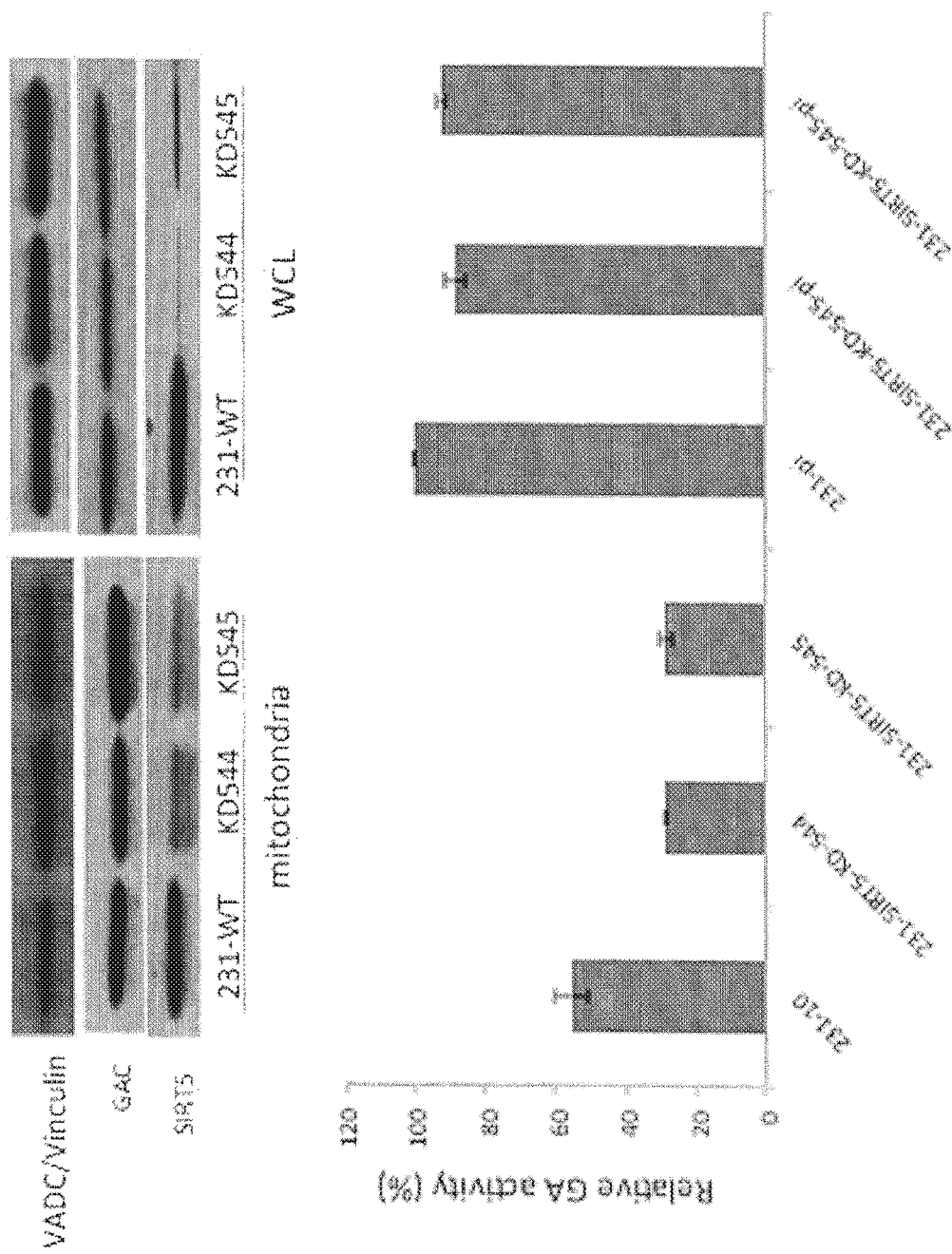
FIG. 5. The knock-down of Sirt5 inhibits GLS1 activation in MDAMB231 cells. Top panel shows the siRNA-mediated knock-down of Sirt5 expression in MDAMB231 cells. The expression levels of GLS1 (labeled as GAC) were unaffected by the knock-down of Sirt5. VADC/Vinculin served as a loading control. Bottom panel: GLS1 activity was assayed in the mitochondrial fractions and whole cell lysates (WCL) from MDAMB231 cells treated with a control RNA or with two siRNAs targeting Sirt5.

The basal GLS1 activity in cancer cells reflects the activation of the enzyme, as non-transformed cells show little or no detectable basal enzyme activity, as is also the case when assaying purified recombinant GLS1 (Wang et al., Cancer Cell 18: 207-209 (2010)). It had been previously shown that the MDAMB231 breast cancer cell line exhibits high levels of basal GLS1 activity. However, as shown in FIG. 5, the siRNA-mediated knock-down of Sirt5 expression was accompanied by a corresponding reduction in the basal GLS1 activity, whereas the levels of GLS1 was essentially not affected when directly assaying GLS1 by adding 100 mM inorganic phosphate. On the other hand, knock-downs of Sirt4, which is also in the mitochondria and has been suggested to regulate GDH activity, resulted in no significant changes in the basal GLS1 activity (not shown).

```
Sirt5 complete CDs (SEQ ID NO: 1), with nucleotides 274 . . . 1206
representing the coding region.
   1 cgcctctagg agaaagcctg gaacgcgtac cggagggtac cagagctctt agcgggccgg 61 cagcatgtgc ggggccaagt aaatggaaat gttttctaac atataaaaac ctacagaaga 121 agaaaataat tttctggatc aaattagaag tctgtattat attgatgtct ccagattcaa 181 atatattaga aagcagccgt ggagacaacc atcttcattt tgggagaaat aactaaagcc 241 cgcctcaagc attagaacta cagacaaacc ctgatgcgac ctctccagat tgtcccaagt 301 cgattgattt cccagctata ttgtggcctg aagcctccag cgtccacacg aaaccagatt 361 tgcctgaaaa tggctcggcc aagttcaagt atggcagatt tcgaaagtt ttttgcaaaa 421 gcaaagcaca tagtcatcat ctcaggagct ggtgttagtg cagaaagtgg tgttccgacc 481 ttcagaggag ctggaggtta ttggagaaaa tggcaagccc aggacctggc gactccctg 541 gcctttgccc acaacccgtc ccgggtgtgg gagttctacc actaccggcg ggaggtcatg 601 gggagcaagg agcccaacgc cgggcaccgc gccatagccg agtgtgagac ccggctgggc 661 aagcagggcc ggcgagtcgt ggtcatcacc cagaacatcg atgagctgca ccgcaaggct 721 ggcaccaaga accttctgga gatccatggt agcttattta aaactcgatg tacctcttgt 781 ggagttgtgg ctgagaatta caagagtcca atttgtccag ctttatcagg aaaaggtgct 841 ccagaacctg gaactcaaga tgccagcatc ccagttgaga aacttccccg gtgtgaagag 901 gcaggctgcg ggggcttgct gcgacctcac gtcgtgtggt ttggagaaaa cctggatcct 961 gccattctgg aggaggttga cagagagctc gcccactgtg atttatgtct agtggtgggc 1021 acttcctctg tggtgtaccc agcaaccatg tttgccccccc aggtggctgc caggggcgtg 1081 ccagtggctg aatttaacac ggagaccacc ccagctacga acagattcag gtttcatttc 1141 cagggaccct gtggaacgac tcttcctgaa gcccttgcct gtcatgaaaa tgaaactgtt 1201 tcttaagtgt cctggggaag aaagaaatta cagtatatct aagaactagg ccacacgcag 1261 aggagaaatg gtcttatggg tggtgagctg agtactgaac aatctaaaaa tagcctctga 1321 ttccctcgct ggaatccaac ctgttgataa gtgatggggg tttagaagta gcaaagagca 1381 cccacattca aaagtcacag aactggaaag ttaattcata ttatttggtt tgaactgaaa 1441 cgtgaggtat ctttgatgtg tatggttggt tattgggagg gaaaaatttt gtaaattaga 1501 ttgtctaaaa aaaatagtta ttctgattat attttttgtta tctgggcaaa gtagaagtca 1561 aggggtaaaa accctactat tctgattttt gcacaagttt tagtggaaaa taaaatcaca 1621 ctctacagta ggt Sirt5 Protein sequence (SEQ ID NO: 2)
MRPLQIVPSRLISQLYCGLKPPASTRNQICLKMARPSSSMADFRKFFAKAKHIVIISGAGVSAESGVPTF

RGAGGYWRKWQAQDLATPLAFAHNPSRVWEFYHYRREVMGSKEPNAGHRAIAECETRLGKQGRRV

VVITQNIDELHRKAGTKNLLEIHGSLFKTRCTSCGVVAENYKSPICPALSGKGAPEPGTQDASIPVEKLPR
```

CEEAGCGGLLRPHVVWFGENLDPAILEEVDRELAHCDLCLVVGTSSVVYPAAMFAPQVAARGVPVAE

FNTETTPATNRFRFHFQGPCGTTLPEALACHENETVS

What is claimed is:

1. A compound that inhibits Sirt5 demalonylase or desuccinylase activity, having the formula:

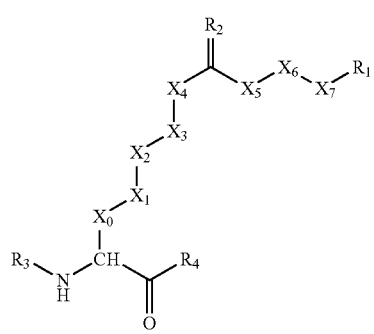

wherein:
$R_1$ is a carboxylate alkyl ester;
$R_2$ is S;
$X_0$, $X_1$, $X_2$, $X_3$, $X_6$, and $X_7$ are each —$CH_2$—;
$X_4$ is —$NR_5$—, wherein $R_5$ is H, methyl, ethyl, isopropyl, phenyl, or benzyl;
$X_5$ is —$CH_2$— or —$NR_5$—;
$R_3$ and $R_4$ are independently selected from H, hydrocarbon (R), amino acid, dipeptide, tripeptide, oligopeptide, protein, nucleobase, nucleotide, dinucleotide, trinucleotide, oligonucleotide, monosaccharide, disaccharide, oligosaccharide, and protecting groups or a combination thereof or modified form thereof.

2. The compound of claim 1, wherein $X_5$ is —$CH_2$—.

3. The compound of claim 1, wherein $R_3$ and $R_4$ are independently selected from amino acid, dipeptide, tripeptide, oligopeptide, and protein.

4. The compound of claim 1, wherein the compound is H3K9 thiosuccinyl peptide.

5. The compound of claim 1, wherein $X_5$ is —$NR_5$—.

* * * * *

SEQUENCE LISTING

<160> NUMBER OF SEQ ID NOS: 14

<210> SEQ ID NO 1
<211> LENGTH: 1633
<212> TYPE: DNA
<213> ORGANISM: Homo sapiens

<400> SEQUENCE: 1

```
cgcctctagg agaaagcctg gaacgcgtac cggagggtac cagagctctt agcgggccgg      60
cagcatgtgc ggggccaagt aaatggaaat gttttctaac atataaaaac ctacagaaga     120
agaaaataat tttctggatc aaattagaag tctgtattat attgatgtct ccagattcaa     180
atatattaga aagcagccgt ggagacaacc atcttcattt tgggagaaat aactaaagcc     240
cgcctcaagc attagaacta cagacaaacc ctgatgcgac ctctccagat tgtcccaagt     300
cgattgattt cccagctata ttgtggcctg aagcctccag cgtccacacg aaaccagatt     360
tgcctgaaaa tggctcggcc aagttcaagt atggcagatt tcgaaagtt ttttgcaaaa      420
gcaaagcaca tagtcatcat ctcaggagct ggtgttagtg cagaaagtgg tgttccgacc     480
ttcagaggag ctggaggtta ttggagaaaa tggcaagccc aggacctggc gactcccctg     540
gcctttgccc acaacccgtc ccgggtgtgg gagttctacc actaccggcg ggaggtcatg     600
gggagcaagg agcccaacgc cgggcaccgc gccatagccg agtgtgagac ccggctgggc     660
aagcagggcc ggcgagtcgt ggtcatcacc cagaacatcg atgagctgca ccgcaaggct     720
ggcaccaaga accttctgga gatccatggt agcttattta aaactcgatg tacctcttgt     780
ggagttgtgg ctgagaatta caagagtcca atttgtccag ctttatcagg aaaaggtgct     840
ccagaacctg gaactcaaga tgccagcatc ccagttgaga acttccccg tgtgtgaagag     900
gcaggctgcg ggggcttgct gcgacctcac gtcgtgtggt ttggagaaaa cctggatcct     960
gccattctgg aggaggttga cagagagctc gcccactgtg atttatgtct agtggtgggc    1020
acttcctctg tggtgtaccc agcagccatg tttgcccccc aggtggctgc caggggcgtg    1080
ccagtggctg aatttaacac ggagaccacc ccagctacga acagattcag gtttcatttc    1140
cagggaccct gtggaacgac tcttcctgaa gcccttgcct gtcatgaaaa tgaaactgtt    1200
tcttaagtgt cctggggaag aaagaaatta cagtatatct aagaactagg ccacacgcag    1260
aggagaaatg gtcttatggg tggtgagctg agtactgaac aatctaaaaa tagcctctga    1320
ttccctcgct ggaatccaac ctgttgataa gtgatggggg tttagaagta gcaaagagca    1380
cccacattca aaagtcacag aactggaaag ttaattcata ttatttggtt tgaactgaaa    1440
cgtgaggtat ctttgatgtg tatggttggt tattgggagg gaaaaatttt gtaaattaga    1500
ttgtctaaaa aaaatagtta ttctgattat attttgtta tctgggcaaa gtagaagtca    1560
agggtaaaa accctactat tctgattttt gcacaagttt tagtggaaaa taaaatcaca    1620
ctctacagta ggt                                                       1633
```

<210> SEQ ID NO 2
<211> LENGTH: 310
<212> TYPE: PRT
<213> ORGANISM: Homo sapiens

<400> SEQUENCE: 2

```
Met Arg Pro Leu Gln Ile Val Pro Ser Arg Leu Ile Ser Gln Leu Tyr
1               5                   10                  15
Cys Gly Leu Lys Pro Pro Ala Ser Thr Arg Asn Gln Ile Cys Leu Lys
            20                  25                  30
Met Ala Arg Pro Ser Ser Met Ala Asp Phe Arg Lys Phe Phe Ala
        35                  40                  45
Lys Ala Lys His Ile Val Ile Ser Gly Ala Gly Val Ser Ala Glu
    50                  55                  60
Ser Gly Val Pro Thr Phe Arg Gly Ala Gly Gly Tyr Trp Arg Lys Trp
65                  70                  75                  80
Gln Ala Gln Asp Leu Ala Thr Pro Leu Ala Phe Ala His Asn Pro Ser
            85                  90                  95
Arg Val Trp Glu Phe Tyr His Tyr Arg Arg Glu Val Met Gly Ser Lys
            100                 105                 110
Glu Pro Asn Ala Gly His Arg Ala Ile Ala Glu Cys Glu Thr Arg Leu
        115                 120                 125
Gly Lys Gln Gly Arg Arg Val Val Val Ile Thr Gln Asn Ile Asp Glu
130                 135                 140
Leu His Arg Lys Ala Gly Thr Lys Asn Leu Leu Glu Ile His Gly Ser
145                 150                 155                 160
Leu Phe Lys Thr Arg Cys Thr Ser Cys Gly Val Val Ala Glu Asn Tyr
                165                 170                 175
Lys Ser Pro Ile Cys Pro Ala Leu Ser Gly Lys Gly Ala Pro Glu Pro
            180                 185                 190
Gly Thr Gln Asp Ala Ser Ile Pro Val Glu Lys Leu Pro Arg Cys Glu
        195                 200                 205
Glu Ala Gly Cys Gly Gly Leu Leu Arg Pro His Val Val Trp Phe Gly
210                 215                 220
Glu Asn Leu Asp Pro Ala Ile Leu Glu Glu Val Asp Arg Glu Leu Ala
225                 230                 235                 240
His Cys Asp Leu Cys Leu Val Val Gly Thr Ser Ser Val Val Tyr Pro
                245                 250                 255
Ala Ala Met Phe Ala Pro Gln Val Ala Ala Arg Gly Val Pro Val Ala
            260                 265                 270
Glu Phe Asn Thr Glu Thr Thr Pro Ala Thr Asn Arg Phe Arg Phe His
        275                 280                 285
Phe Gln Gly Pro Cys Gly Thr Thr Leu Pro Glu Ala Leu Ala Cys His
    290                 295                 300
Glu Asn Glu Thr Val Ser
305                 310
```

<210> SEQ ID NO 3
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 3
ccagcgucca cacgaaacca gauuu                                      25

<210> SEQ ID NO 4
<211> LENGTH: 25
<212> TYPE: RNA

```
<213> ORGANISM: Artificial Sequence
<220> FEATURE:
<223> OTHER INFORMATION: Synthetic Oligonucleotide

<400> SEQUENCE: 4
aaaucugguu ucugggugac gcugg                                            25

<210> SEQ ID NO 5
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 5
ccaagucgau ugauuuccca gcuau                                            25

<210> SEQ ID NO 6
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 6
auagcuggga aaucaaucga cuugg                                            25

<210> SEQ ID NO 7
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 7
ugcaaaagca aagcacauag ucauc                                            25

<210> SEQ ID NO 8
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 8
gaugacuaug ugcuuugcuu uugca                                            25

<210> SEQ ID NO 9
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 9
acccgucccg ggugugggag uucua                                            25

<210> SEQ ID NO 10
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 10
uagaacuccc acacccggga cgggu                                            25
```

```
<210> SEQ ID NO 11
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 11
cucgauguac cucuugugga guugu                                         25

<210> SEQ ID NO 12
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 12
acaacuccac aagagguaca ucgag                                         25

<210> SEQ ID NO 13
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 13
aaacuucccc ggugugaaga ggcag                                         25

<210> SEQ ID NO 14
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 14
cugccucuuc acaccgggga aguuu                                         25
```